United States Patent
Komasaka

(10) Patent No.: US 12,369,878 B2
(45) Date of Patent: Jul. 29, 2025

(54) RADIATION DETECTING APPARATUS, RADIOGRAPHIC IMAGING SYSTEM, AND INCLINATION ANGLE OUTPUTTING METHOD

(71) Applicant: Konica Minolta, Inc., Tokyo (JP)

(72) Inventor: Tomonori Komasaka, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 254 days.

(21) Appl. No.: 18/057,264

(22) Filed: Nov. 21, 2022

(65) Prior Publication Data

US 2023/0165551 A1 Jun. 1, 2023

(30) Foreign Application Priority Data

Dec. 1, 2021 (JP) ................. 2021-195072

(51) Int. Cl.
*A61B 6/00* (2024.01)
*A61B 6/58* (2024.01)
*A61B 6/08* (2006.01)
*A61B 6/42* (2024.01)

(52) U.S. Cl.
CPC ............. *A61B 6/547* (2013.01); *A61B 6/587* (2013.01); *A61B 6/08* (2013.01); *A61B 6/4283* (2013.01)

(58) Field of Classification Search
CPC ........ A61B 6/547; A61B 6/4429; A61B 6/587
See application file for complete search history.

(56) References Cited

U.S. PATENT DOCUMENTS

2022/0183650 A1* 6/2022 Saito ................... A61B 6/4283

FOREIGN PATENT DOCUMENTS

| CN | 111096759 A | 5/2020 |
|---|---|---|
| JP | 2017-164425 A | 9/2017 |
| JP | 6552619 B2 | 7/2019 |
| JP | 2020-039526 A | 3/2020 |
| WO | 2017/013849 A1 | 1/2017 |

OTHER PUBLICATIONS

JP 2022-093760 A (JP App. No. 2020-206390) with a machine English translation (Year: 2022).*
Office Action, dated Mar. 11, 2025, issued for the corresponding Japanese Patent Application No. 2021-195072, 12 pages, with English translation.

* cited by examiner

*Primary Examiner* — Chih-Cheng Kao
(74) *Attorney, Agent, or Firm* — LUCAS & MERCANTI, LLP

(57) ABSTRACT

A radiation detecting apparatus detects radiation transmitted through a subject. The radiation detecting apparatus includes a hardware processor. The hardware processor detects rotation angles of the radiation detecting apparatus with respect to two mutually perpendicular axes to output angle information, and also detects an orientation of the radiation detecting apparatus. The hardware processor outputs the angle information for the detected orientation.

10 Claims, 10 Drawing Sheets

UPWARD IF $|Ax| \leq |Ay|$
AND $Ay \geq 0$

DOWNWARD IF $|Ax| \leq |Ay|$
AND $Ay < 0$

90° TO LEFT IF $|Ax| > |Ay|$
AND $Ax > 0$

90° TO RIGHT IF $|Ax| > |Ay|$
AND $Ax \leq 0$

FIG.8A
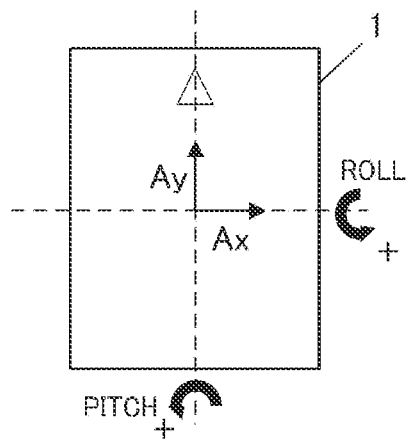
UPWARD
FIG.8B
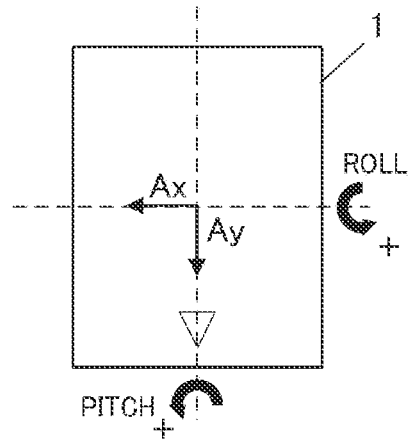
DOWNWARD
FIG.8C
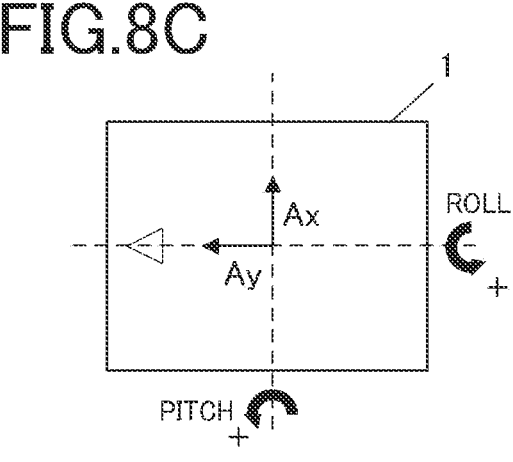
90° TO LEFT
FIG.8D
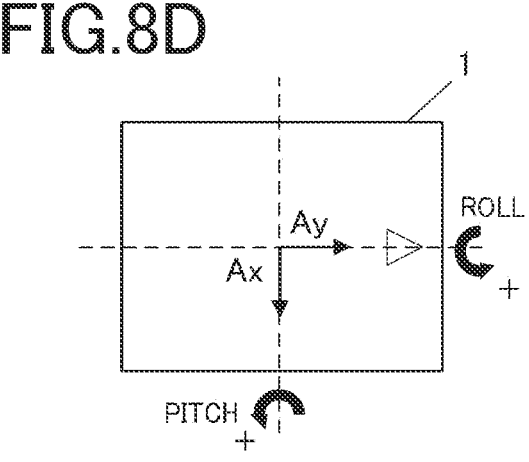
90° TO RIGHT
FIG.9
| ORIENTATION OF DETECTING APPARATUS | ROLL | PITCH |
|---|---|---|
| UPWARD | $\theta$ | $\phi$ |
| DOWNWARD | $-\theta$ | $-\phi$ |
| 90° TO LEFT | $\phi$ | $-\theta$ |
| 90° TO RIGHT | $-\phi$ | $\theta$ |

ROLL ANGLE 40°
PITCH ANGLE 0°

ROLL ANGLE 0°
PITCH ANGLE 40°

ROLL ANGLE −40°
PITCH ANGLE 0°

RADIATION DETECTING APPARATUS, RADIOGRAPHIC IMAGING SYSTEM, AND INCLINATION ANGLE OUTPUTTING METHOD

CROSS-REFERENCE TO RELATED APPLICATIONS

The entire disclosure of Japanese Patent Application No. 2021-195072 filed on Dec. 1, 2021 is incorporated herein by reference in its entirety.

TECHNICAL FIELD

The present disclosure relates to a radiation detecting apparatus, a radiographic imaging system, and an inclination angle outputting method.

DESCRIPTION OF THE RELATED ART

A mobile radiographic imaging system, called nursing cart, may be used to perform radiographic imaging of an examinee who is, for example, on a bed in a ward of a hospital.

In imaging of an examinee on a bed, an imaging surface of a portable (panel-shaped) radiation detecting apparatus that is placed between the back of the examinee and the bed is not always parallel or perpendicular (i.e., may be inclined) to the horizontal plane.

It is necessary to adjust the orientation of a tube with respect to the radiation detecting apparatus such that the radiation emission axis of the tube is perpendicular to the imaging surface of the radiation detecting apparatus in order to, in the above case too, prevent density difference in a radiograph due to cutoff by a grid from being generated, the grid being attached to a radiation incident surface of the radiation detecting apparatus, and prevent change in positional relationship between structures in the body of the examinee captured in the radiation detecting apparatus from affecting diagnosis.

Then, there have been proposed various techniques to assist users in adjusting the orientation of a tube.

For example, in JP 6552619 B2, there is disclosed a technique of providing a radiation emitting apparatus with a changing unit that changes orientation (direction) of a radiation source (tube), wherein, in the case where inclination and rotation angle of a monitor are controlled on the basis of the orientation and rotation angle of a radiation detecting apparatus, the changing unit controls the orientation of the radiation source on the basis of the inclination of the radiation detecting apparatus.

However, with the technique disclosed in JP 6552619 B2, roll angle and pitch angle of the radiation source (tube) can be aligned with the roll angle and the pitch angle of the radiation detecting apparatus in one orientation of the radiation detecting apparatus only. That is, as shown in FIG. 14, the roll angle and the pitch angle of the radiation detecting apparatus are defined in one orientation (e.g., upward) of the radiation detecting apparatus, so that, for example, in the case where imaging is performed with the radiation detecting apparatus rotated 90 degrees to the left (shown in FIG. 15B) from the above one orientation (shown in FIG. 15A), the roll angle and the pitch angle of the radiation source (tube) and the roll angle and the pitch angle of the radiation detecting apparatus have kind of a reversed relationship, which causes a problem in angle adjustment of the radiation source (tube) and the radiation detecting apparatus.

SUMMARY OF THE INVENTION

The present disposure has been made in view of the above problem(s), and objects thereof include easily performing angle adjustment of a tube and a radiation detecting apparatus.

In order to achieve at least one of the abovementioned objects, according to a first aspect of the present disclosure, there is provided a radiation detecting apparatus that detects radiation transmitted through a subject, including a hardware processor that
  detects rotation angles of the radiation detecting apparatus with respect to two mutually perpendicular axes to output angle information, and
  detects an orientation of the radiation detecting apparatus,
  wherein the hardware processor outputs the angle information for the detected orientation.

In order to achieve at least one of the abovementioned objects, according to a second aspect of the present disclosure, there is provided a radiographic imaging system including:
  a radiation emitting apparatus that emits radiation;
  a radiation detecting apparatus that detects the radiation transmitted through a subject; and
  a hardware processor that
    detects rotation angles of the radiation detecting apparatus with respect to two mutually perpendicular axes to output angle information, and
    detects an orientation of the radiation detecting apparatus,
  wherein the hardware processor outputs the angle information for the detected orientation, and
  wherein the hardware processor causes a display to display the output angle information.

In order to achieve at least one of the abovementioned objects, according to a third aspect of the present disclosure, there is provided an inclination angle outputting method for a radiation detecting apparatus that detects radiation transmitted through a subject, including:
  (i) detecting rotation angles of the radiation detecting apparatus with respect to two mutually perpendicular axes to output angle information; and
  (ii) detecting an orientation of the radiation detecting apparatus,
  wherein the (i) detecting includes outputting the angle information for the detected orientation.

BRIEF DESCRIPTION OF THE DRAWINGS

The accompanying drawings are not intended as a definition of the limits of the present disclosure but illustrate embodiments of the present disclosure, and together with the general description given above and the detailed description of the embodiments given below, serve to explain the principles of the present disclosure, wherein:

FIG. 8A to FIG. 8D are illustrations to explain a relationship between the orientation of the radiation detecting apparatus and roll and pitch thereof;

FIG. 9 is a table showing the relationship between the orientation of the radiation detecting apparatus and the roll and the pitch thereof;

DETAILED DESCRIPTION

Hereinafter, one or more embodiments of the present disclosure will be described with reference to the drawings. However, the technical scope of the present disclosure is not limited to the embodiments below or illustrated examples.

1. Radiographic Imaging System

First, a schematic configuration of a radiographic imaging system (hereinafter "system 100") according to an embodiment(s) will be described using a case where the system 100 constitutes a nursing cart.

Figure 1:
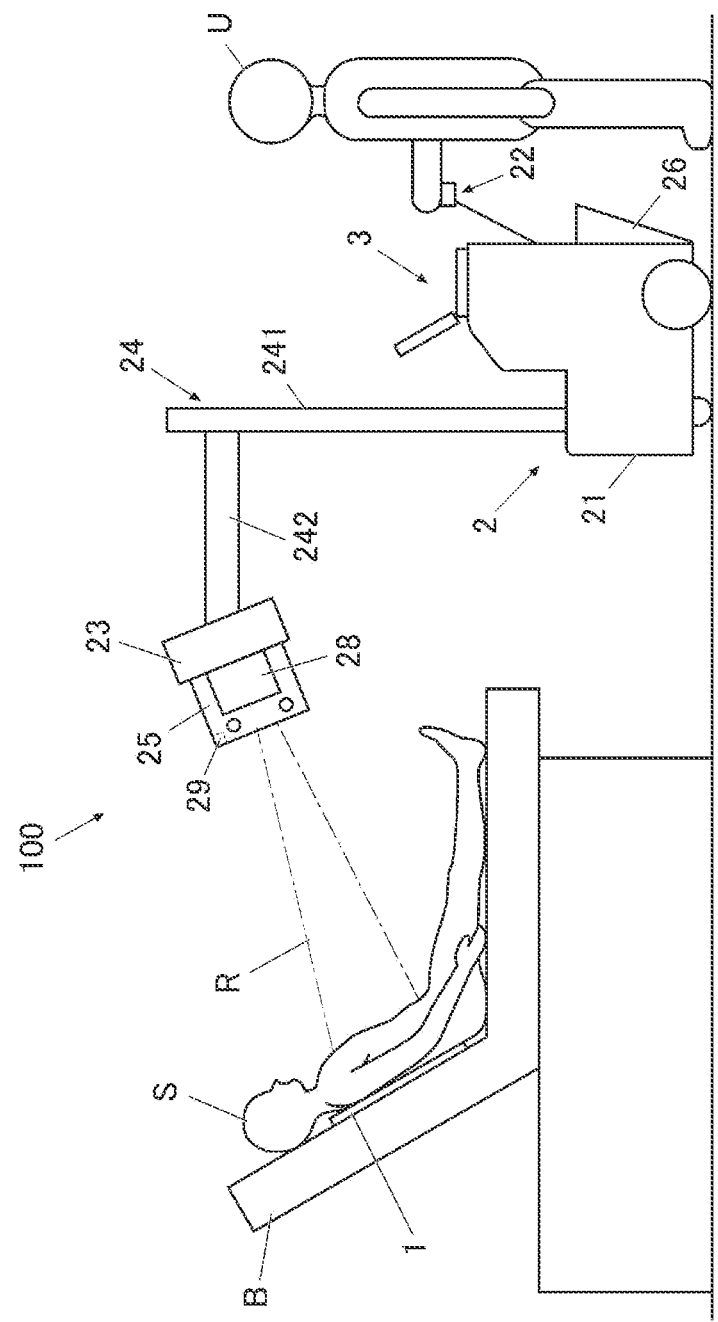
FIG. 1 is a side view showing an example of a radiographic imaging system according to an embodiment(s)
Figure 2:
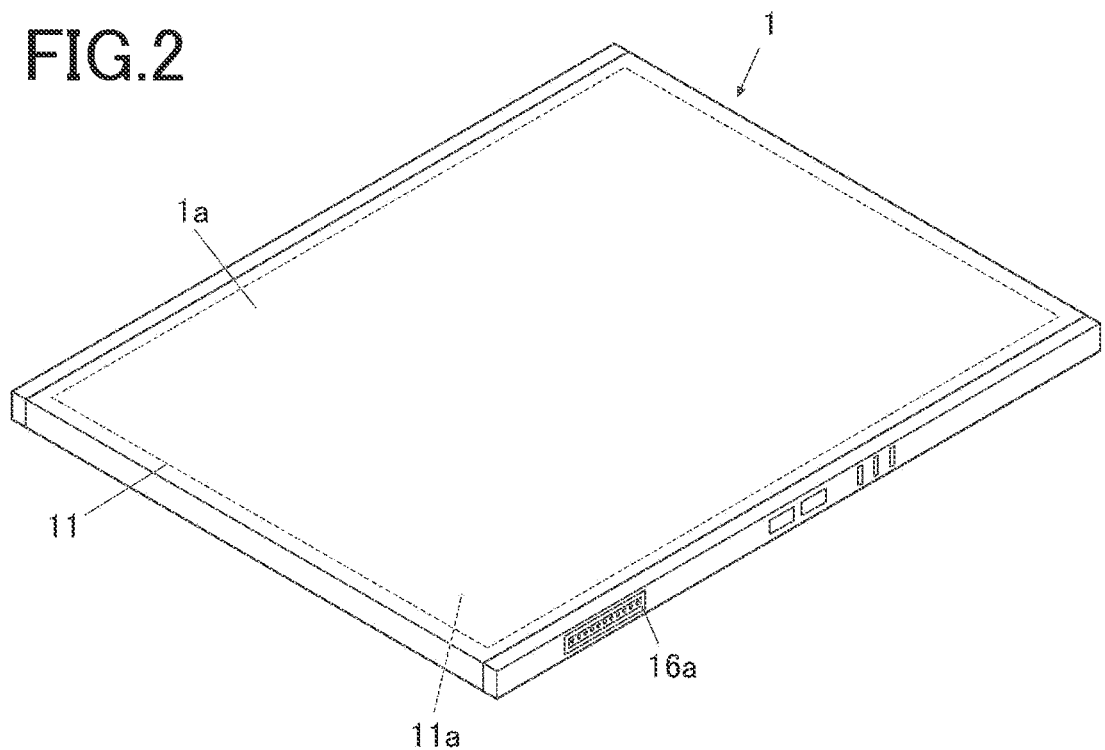
FIG. 2 is a perspective view of a radiation detecting apparatus included in the radiographic imaging system shown in FIG. 1.

FIG. 1 shows the system 100, and FIG. 2 is a perspective view of a radiation detecting apparatus 1 included in the system 100.

As shown in FIG. 1, the system 100 includes a radiation detecting apparatus (hereinafter "detecting apparatus 1"), a radiation generating apparatus (or radiation emitting apparatus, hereinafter "generating apparatus 2") and a console 3.

The apparatuses 1 to 3 can communicate with one another via, for example, a communication network, such as a LAN (Local Area Network), a WAN (Wide Area Network) or Internet.

The system 100 may be capable of communicating with a hospital information system (HIS), a radiology information system (RIS), a picture archiving and communication system (PACS), a dynamic analysis apparatus and so forth (all not shown).

The communication network may be a network using cables or a wireless network.

[1-1. Radiation Detecting Apparatus]

The detecting apparatus 1 generates a radiograph(s) according to radiation R received from the generating apparatus 2.

As shown in FIG. 1 and FIG. 2, the detecting apparatus 1 of this embodiment is panel-shaped and can be carried around.

Hence, the detecting apparatus 1 of this embodiment can be used by being mounted on an imaging stand, by being horizontally placed between a bed B and a subject (examinee) S who is in a decubitus position on the bed B, or as shown in FIG. 1, by being placed to stand between the subject S who is in a sitting (or reclining) position on the bed B that partially stands or in a wheelchair and the backrest part of the bed B or the wheelchair.

Although a radiation incident surface 1a (surface facing the subject S) of the detecting apparatus 1 mounted on an imaging stand is parallel or perpendicular to the horizontal plane, the radiation incident surface 1a is not always parallel or perpendicular to the horizontal plane (i.e., may be inclined thereto) in imaging not using an imaging stand (e.g., the subject S is on the bed B or in a wheelchair).

The detecting apparatus 1 may move with motion (body movement) of the subject S when it is interposed between a soft article, such as the bed B, and the subject S.

Details of the detecting apparatus 1 will be described later.

[1-2. Radiation Generating Apparatus]

As shown in FIG. 1, the generating apparatus 2 includes a main body 21, an emission instructing switch 22 and a tube 23.

The generating apparatus 2 of this embodiment further includes a tube support 24, a collimator 25 and a detecting apparatus storage 26.

The generating apparatus 2 of this embodiment is provided with wheels on its case, thereby being movable.

Details of the main body 21 will be described later.

[1-2-1. Emission Instructing Switch]

The emission instructing switch 22 outputs an operation signal(s) to the main body 21 by being operated (pressed) by a user U.

Although FIG. 1 shows an example in which the emission instructing switch 22 is connected to the main body 21 with a cable, the emission instructing switch 22 may be connected to the main body 21 wirelessly.

[1-2-2. Tube]

The tube 23 generates a dose of radiation R (e.g., X-rays, etc.) according to preset imaging conditions in a mode suitable for the imaging conditions to emit same from its emission port, in response to an operation on the emission instructing switch 22.

[1-2-3. Tube Support]

The tube support 24 supports the tube 23.

The tube support 24 of this embodiment includes a first support part 241 extending upward from the main body 21 and a second support part 242 extending forward from the upper portion of the first support part 241.

The tip of the second support part 242 supports the tube 23.

The tube support 24 further includes a not-shown joint mechanism to move the tube 23 in the X-axis direction (front-back direction of the generating apparatus 2, i.e., left-right direction in FIG. 1), the Y-axis direction (width direction of the generating apparatus 2, i.e., direction perpendicular to the paper surface of FIG. 1) perpendicular to the X-axis, and the Z-axis direction (vertical direction, i.e., up-down direction in FIG. 1) perpendicular to the X-axis and the Y-axis.

The tube support 24 can change the orientation of the emission port, from which radiation R is emitted, by rotating, with the not-shown joint mechanism, the tube 23 on rotational axes parallel to the X-, Y- and Z-axes.

[1-2-4. Collimator]

The collimator 25 is attached to the emission port of the tube 23 and narrows radiation R such that an irradiation field with the radiation R emitted from the emission port becomes a preset rectangular shape.

The collimator 25 includes a not-shown lamp button.

By the lamp button being operated by the user U, visible light is emitted to an area that is the irradiation field with the radiation R.

[1-2-5. Detecting Apparatus Storage]

The detecting apparatus storage 26 stores the detecting apparatus 1 when the detecting apparatus 1 is not in use.

The detecting apparatus storage 26 of this embodiment is disposed on/in the lateral surface of the main body 21.

The detecting apparatus storage 26 of this embodiment can store a plurality of detecting apparatuses 1.

In the detecting apparatus storage 26, a not-shown connector is disposed, and when the detecting apparatus 1 is stored therein, the not-shown connector is connected to a connector 16a of the detecting apparatus 1.

[1-3. Console]

The console 3 is constituted by a PC, a portable terminal or a dedicated apparatus.

As shown in FIG. 1, the console 3 of this embodiment is mounted on the generating apparatus 2.

The console 3 can set the imaging conditions (tube voltage, tube current and emission time or current-time product (mAs value), imaging part, imaging direction, etc.) in at least one of the detecting apparatus 1 and the generating apparatus 2 on the basis of an imaging order(s) obtained from another system (HIS, RIS, etc.) or an operation(s) made on an operation unit 32 by the user U (e.g., radiologist).

The console 3 can obtain image data of a radiograph(s) generated by the detecting apparatus 1, and store it in itself or send it to another apparatus (PACS, dynamic analysis apparatus, etc.).

[1-4. Outline of Radiographic Imaging using Radiographic Imaging System]

Radiographic imaging (imaging of the subject S in a sitting position) using the system 100 (nursing cart) thus configured is performed as follows.

First, the system 100 is placed beside the subject S (near the bed B or a wheelchair).

Next, the subject S is gotten to take a sitting position. If the subject S sits on an angle-adjustable article (e.g., the bed B capable of being partially stood), the angle of the backrest part thereof is adjusted as appropriate.

Next, the position and the orientation of the tube 23 are roughly adjusted such that the emission port of the tube 23 faces the imaging part of the subject S.

Next, the detecting apparatus 1 is taken out from the detecting apparatus storage 26 and placed between the back of the subject S and the backrest part.

Next, with reference to inclination information (detailed later), the orientation of the tube 23 and the irradiation field are finely adjusted such that the emission axis of radiation R is perpendicular to the radiation incident surface 1a.

Next, imaging is performed (radiation R is emitted to the diagnostic part (imaging part) of the subject S so that the detecting apparatus 1 generates a radiograph(s) (still image or dynamic image) in which the diagnostic part is captured).

If a dynamic image is generated, image data of the dynamic image is sent to a dynamic analysis apparatus as needed for analysis of the dynamic state of the imaging part (ventilation function/blood flow state of lungs, bending and stretching of joints, etc.).

[1-5. Modification of Radiographic Imaging System]

The main body 21 and the console 3 may be integrated (i.e., stored in a single case).

The generating apparatus 2 may be movable by means other than wheels. For example, the generating apparatus 2 may be light enough to be carried around by a person or mounted on a commercially available cart or the like, or may have a smooth bottom surface that slides on a floor.

The system 100 may be a system in which one of the detecting apparatus 1 and the generating apparatus 2 is installed, for example, in an imaging room of a medical facility (and the other is freely movable).

2. Details of Radiation Detecting Apparatus

Next, details of the detecting apparatus 1 included in the system 100 will be described.

Figure 3:
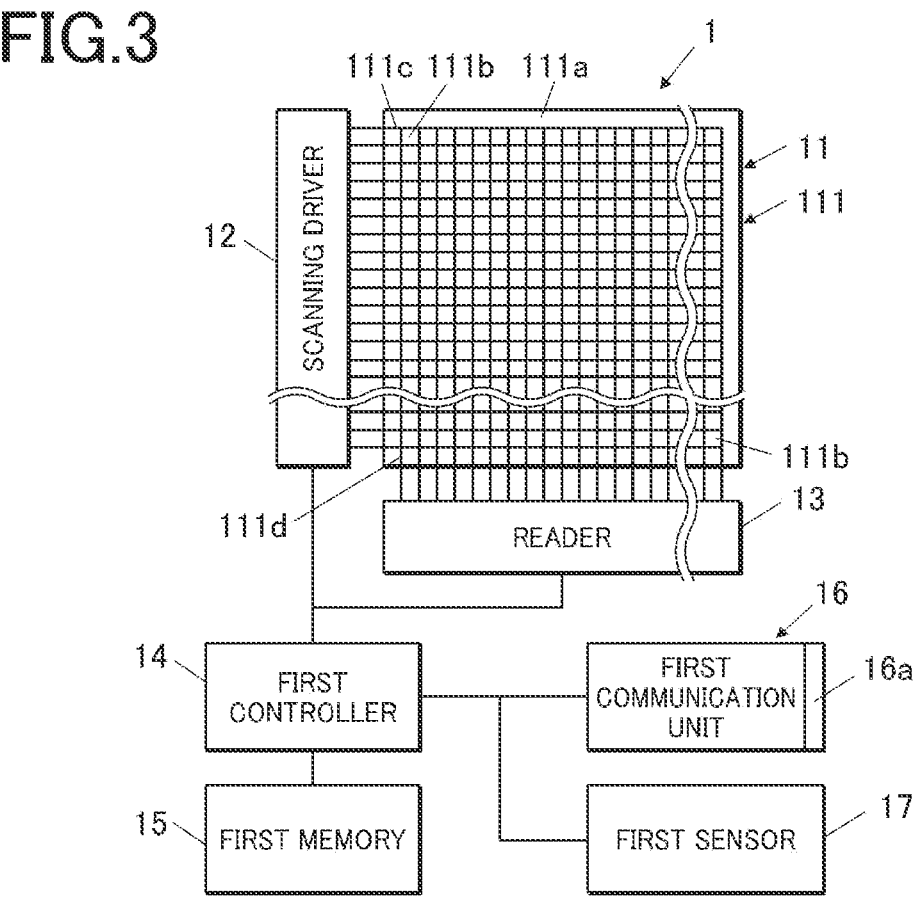
FIG. 3 is a block diagram of the radiation detecting apparatus shown in FIG. 2.

FIG. 3 is a block diagram showing an electrical configuration of the detecting apparatus 1.

[2-1. Specific Configuration of Radiation Detecting Apparatus]

As shown in FIG. 3, the detecting apparatus 1 includes a radiation detector 11, a scanning driver 12, a reader 13, a first controller 14 (hardware processor), a first memory 15, a first communication unit 16 and a first sensor 17.

The components 11 to 17 are electrically connected to one another.

[2-1-1. Radiation Detector]

The radiation detector 11 includes a not-shown scintillator and a photoelectric conversion panel 111.

The scintillator is plate-shaped and made of, for example, columnar CsI crystals.

By receiving radiation R, the scintillator emits, with an intensity corresponding to the dose (mAs) of the received radiation R, electromagnetic waves of a longer wavelength (e.g., visible light) than the radiation R.

The scintillator is disposed so as to spread parallel to the radiation incident surface 1a (shown in FIG. 2) of the case of the detecting apparatus 1.

The photoelectric conversion panel 111 is disposed on, of the scintillator, the surface opposite the surface facing the radiation incident surface 1a so as to spread parallel to the scintillator.

The photoelectric conversion panel 111 includes a substrate 111a and a plurality of charge accumulators 111b.

The charge accumulators 111b are arranged on, of the substrate 111a, the surface facing the scintillator two dimensionally (e.g., in a matrix). The charge accumulators 111b correspond to respective pixels of a radiograph.

The charge accumulators 111b have semiconductor elements and switch elements. The semiconductor elements generate electric charges of an amount corresponding to the intensity of the electromagnetic waves generated by the scintillator. The switch elements are disposed between the respective semiconductor elements and lines connected to the reader 13.

Bias voltage is applied to each semiconductor element from a not-shown power supply circuit.

By each switch element switching between ON state and OFF state, its corresponding charge accumulator 111b accumulates and releases an electric charge(s), which is read out as a signal value, according to radiation R received.

[2-1-2. Scanning Driver]

The scanning driver 12 applies ON voltage or OFF voltage to each scan line 111c of the radiation detector 11, thereby being capable of switching each switch element to ON state or OFF state.

[2-1-3. Reader]

The reader 13 reads out the amounts of electric charges flowing in from the charge accumulators 111b via signal lines 111d of the radiation detector 11 as signal values.

The reader 13 may perform binning when reading out the signal values.

[2-1-4. First Controller]

The first controller 14 includes a not-shown CPU (Central Processing Unit) and a not-shown RAM (Random Access Memory).

The CPU reads various process programs stored in the first memory 15, loads them to the RAM, and performs various processes in accordance with the process programs, thereby centrally controlling operation of the components of the detecting apparatus 1.

The first controller 14 generates image data of a radiograph on the basis of the signal values read out by the reader 13.

[2-1-5. First Memory]

The first memory 15 is constituted by an HDD (Hard Disk Drive), a semiconductor memory and/or the like.

The first memory 15 stores various programs that are executed by the first controller 14, and parameters, files and so forth necessary for execution of the programs.

The first memory 15 may be capable of storing image data of radiographs.

[2-1-6. First Communication Unit]

The first communication unit 16 is constituted by a communication module and/or the like.

The first communication unit 16 can send and receive various signals and various data to and from other apparatuses (generating apparatus 2, console 3, etc.) connected thereto with cables or wirelessly via a communication network.

[2-1-7. First Sensor]

The first sensor 17 detects information necessary to calculate the abovementioned inclination information.

The first sensor 17 of this embodiment is a three-axis acceleration sensor.

The three-axis acceleration sensor detects accelerations acting in directions of three axes (X-, Y- and Z-axes) as the information necessary to calculate the inclination information and sends same to the first controller 14.

On the three-axis acceleration sensor in a stationary state, only gravitational acceleration acts. Hence, the three-axis acceleration sensor in the stationary state detects three-axis directional components of gravitational acceleration.

The first sensor 17 may be a six-axis sensor or a nine-axis sensor.

The six-axis sensor is composed of the abovementioned three-axis acceleration sensor provided with a function to detect angular velocities (gyro) of three axes.

The nine-axis sensor is composed of the abovementioned six-axis sensor provided with a function to detect points of the compass (east, west, north, south) of three axes.

[2-2. Specific Operation of Radiation Detecting Apparatus]

The first controller 14 of the detecting apparatus 1 thus configured performs the following operations.

[2-2-1. Detection of Acceleration]

The first controller 14 causes the first sensor 17 to repeatedly detect the three-axis directional components of gravitational acceleration in response to a predetermined condition being satisfied.

Examples of the predetermined condition include a condition that the detecting apparatus 1 is powered, a condition that a predetermined control signal is received from another apparatus (generating apparatus 2, console 3, etc.), and a condition that a predetermined operation is made on an operation unit of the detecting apparatus 1.

[2-2-2. Generation and Sending of Radiograph]

The first controller 14 performs control in sync with emission of radiation R from the generating apparatus 2 to cause the scanning driver 12 to accumulate and release electric charges at the radiation detector 11.

The first controller 14 performs control to cause the reader 13 to read out signal values based on the electric charges released by the radiation detector 11.

The first controller 14 generates a radiograph according to dose distribution of the emitted/received radiation R on the basis of the signal values read out by the reader 13.

In the case of generation of still images, one radiograph is generated by one press on the emission instructing switch 22.

In the case of generation of dynamic images, a frame of a dynamic image is generated repeatedly, to be more specific, multiple times per predetermined time (e.g., 15 times per second) by one press on the emission instructing switch 22.

The first controller 14 sends image data of the generated radiograph(s) to another apparatus (console 3, dynamic analysis apparatus, etc.) via the first communication unit 16.

[2-3. First Modification of Radiation Detecting Apparatus]

The radiation detector 11 of the detecting apparatus 1 may directly generate electric charges by the semiconductor elements thereof receiving radiation R, without being provided with the scintillator.

The detecting apparatus 1 may not generate image data of a dynamic image, but display the dynamic image (e.g., in the form of fluoroscopic X-ray image) in real time on a display apparatus connected to itself.

[2-4. Second Modification of Radiation Detecting Apparatus]

An output value(s) of the first sensor 17 (three-axis acceleration sensor) of the detecting apparatus 1 may indicate a slight inclination even when the radiation incident surface 1a is parallel to an ideal horizontal plane by being affected by the state of the first sensor 17 mounted on the substrate 111a of the radiation detector 11 or the like, the state of the radiation detector 11 attached into the detecting apparatus 1, and/or distortion of the case of the detecting apparatus 1, for example.

Also, when shock is applied to the detecting apparatus 1 (e.g., by the detecting apparatus 1 being dropped, etc.) while the detecting apparatus 1 is being carried around, any of the above states or the like, which cause the output value to indicate an inclination, may nearly occur, or the degree of the state(s) or the like may change.

Hence, the first controller 14 may correct (calibrate) the detection value (output value) of the first sensor 17 that is output to the generating apparatus 2.

More specifically, the first controller 14 corrects the output value so as to indicate no inclination when the detecting apparatus 1 is placed on an ideal horizontal plane/surface.

Alternatively or additionally, the first controller 14 corrects the output value so as to indicate an inclination angle(s) when the detecting apparatus 1 is stored in a place that is inclined at the inclination angle with respect to an ideal horizontal plane (e.g., stored in the detecting apparatus storage 26 of the nursing cart).

The first controller 14 then stores corrected data obtained by the correction in the first memory 15.

The correction is performed, for example, when the detecting apparatus 1 is first set up, after shock is applied to the detecting apparatus 1, or when no corrected data is stored in the first memory 15 of the detecting apparatus 1.

The first controller 14 may automatically perform the correction when detecting that the detecting apparatus 1 is stored in the detecting apparatus storage 26.

Further, the first controller 14 may prompt the user U to perform the correction (e.g., by performing control to display prompting letters/text). In this case, the first controller 14 may prompt the user U to perform the correction only if the first controller 14 determines that the degree of deviation of calculated first angle information (described later) from a prescribed value(s) of the rotation angle(s) of the detecting apparatus 1 with respect to the horizontal plane, the detecting apparatus 1 being stored in the detecting apparatus storage 26, exceeds an allowable range.

3. Details of Radiation Generating Apparatus and Console

Next, details of the generating apparatus 2 and the console 3 included in the system 100 will be described.

[3-1. Specific Configuration of Radiation Generating Apparatus]

Figure 4:
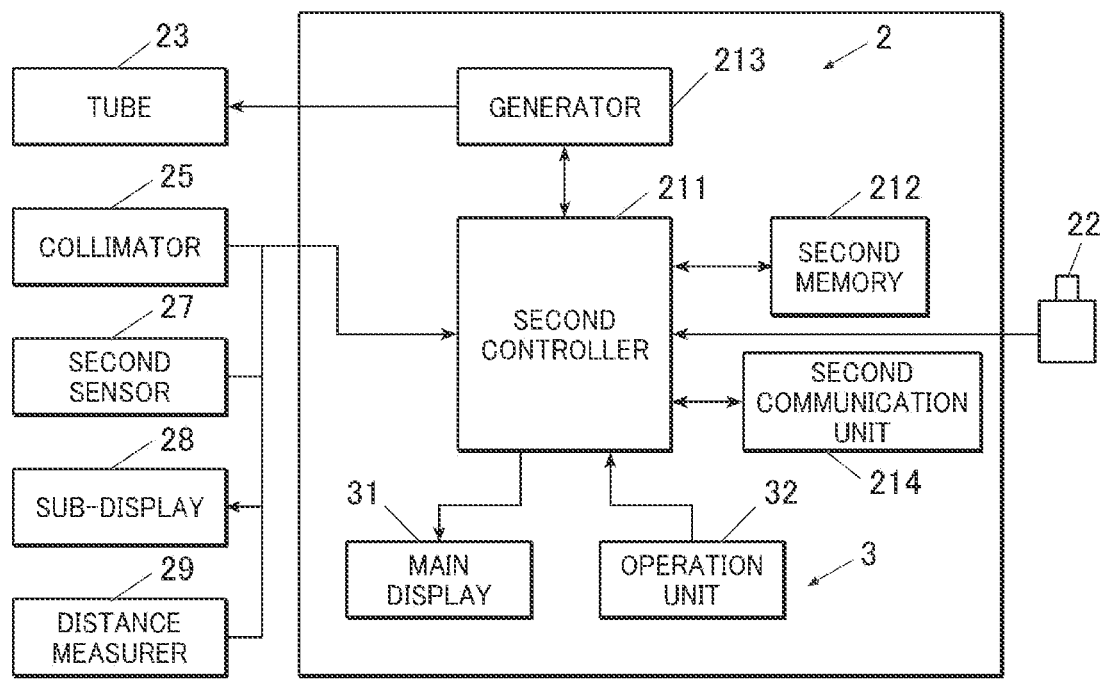
FIG. 4 is a block diagram of a radiation generating apparatus and a console included in the radiographic imaging system shown in FIG. 1.

The generating apparatus 2 includes, in addition to the abovementioned main body 21, emission instructing switch 22, tube 23, tube support 24, collimator 25 and detecting apparatus storage 26, a second sensor 27, a sub-display 28 and a distance measurer 29 as shown in FIG. 4.

The main body 21 of the generating apparatus 2 includes a second controller 211, a second memory 212, a generator 213 and a second communication unit 214.

The components 22, 23, 25, 27, 28, 211-214 are electrically connected to one another by a bus or the like.

[3-1-1. Second Sensor]

The second sensor 27 of this embodiment is a three-axis acceleration sensor, which is the same as the first sensor 17.

The second sensor 27 may be a six-axis sensor or a nine-axis sensor.

The sensor constituting the second sensor 27 may be different in type from the sensor constituting the first sensor 17.

[3-1-2. Sub-Display]

The sub-display 28 is constituted by a monitor, such as an LCD (Liquid Crystal Display) or a CRT (Cathode Ray Tube).

The sub-display 28 displays various images, various types of information and so forth in accordance with instructions of display signals input from the second controller 211.

The sub-display 28 of this embodiment is disposed on the case of the collimator 25.

The sub-display 28 may be disposed on the case of the tube 23 or on the tube support 24.

[3-1-3. Distance Measurer]

The distance measurer 29 measures SID or SSD.

The SID (source image distance) is distance between the focal point F of radiation R and an imaging surface 11a (surface where the charge accumulators 111b of the radiation detector 11 are disposed).

The SSD (source skin distance) is distance between the focal point F of radiation R and the body surface of the subject S, and is approximately equal to difference between the SID and the body thickness of the subject S.

The distance measurer 29 is disposed on/in the collimator 25.

The distance measurer 29 may be constituted, for example, by a light emitter that emits laser light, a detector that detects reflected laser light and a calculator that calculates distance from the light emitter to the reflection point on the basis of time from emission of the laser light to detection of the reflected laser light, or by an optical camera that images the detecting apparatus 1 disposed in the emission direction of radiation R and a calculator that calculates the SID on the basis of an optical image of the detecting apparatus 1 generated by the optical camera and size information on the detecting apparatus 1, or by combination of these.

Since the laser light is reflected by the body surface of the subject S, the distance measured by the distance measurer 29 using the laser light is often the SSD. In this case, the sum of the measured SSD and the body thickness of the subject S is regarded as the SID.

The body thickness may be a predetermined reference value or a numerical value input by the user U, or may be automatically calculated from information on the subject S.

[3-1-4. Second Controller]

The second controller 211 includes a CPU and a RAM.

The CPU of the second controller 211 reads various programs stored in the second memory 212, loads them to the RAM, and performs various processes in accordance with the loaded programs, thereby centrally controlling operation of the components of the generating apparatus 2.

[3-1-5. Second Memory]

The second memory 212 is constituted by a nonvolatile semiconductor memory, a hard disk and/or the like.

The second memory 212 stores various programs that are executed by the second controller 211, and parameters, files and so forth necessary for execution of the programs.

[3-1-6. Generator]

The generator 213 applies voltage and flows current according to the preset imaging conditions to the tube 23 in response to receiving an emission instruction signal from the second controller 211.

[3-1-7. Second Communication Unit]

The second communication unit 214 is constituted by a communication module and/or the like.

The second communication unit 214 can send and receive various signals and various data to and from other apparatuses (detecting apparatus 1, console 3, etc.) connected thereto with cables or wirelessly via a communication network.

[3-2. Specific Configuration of Console]

The console 3 includes a controller, a memory, a communication unit, a main display 31 and the abovementioned operation unit 32.

The controller, the memory and the communication unit of the console 3 of this embodiment are doubled by the second controller 211, the second memory 212 and the second communication unit 214 of the generating apparatus 2, respectively.

The console 3 may include a dedicated controller, a dedicated memory and a dedicated communication unit.

[3-2-1. Main Display]

The main display 31 is constituted by a monitor, such as an LCD or a CRT.

The main display 31 displays various images, various types of information and so forth in accordance with instructions of display signals input from the second controller 211.

[3-2-2. Operation Unit]

The operation unit 32 is operable by the user U.

The operation unit 32 includes a keyboard (cursor keys, numeric input keys, various function keys, etc.), a pointing device (mouse, etc.) and a touchscreen overlaid on the surface of the main display 31.

The operation unit 32 outputs, to the second controller 211, control signals corresponding to operations made by the user U thereon.

[3-3. Specific Operation of Radiographic Imaging System]

The system 100 thus configured performs the following operations (processes).

[3-3-1. Calculation of Inclination Information]

Figure 5:
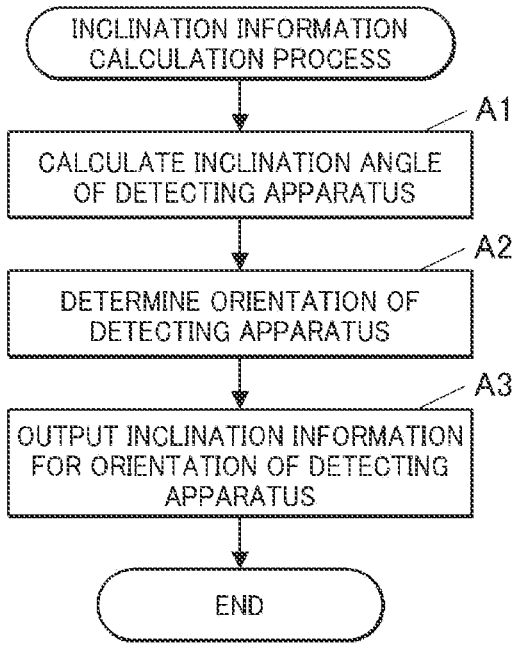
FIG. 5 is a flowchart of an inclination information calculation process that is performed by the radiation detecting apparatus shown in FIG. 3.

The first controller 14 of the detecting apparatus 1 performs, for example, an inclination information calculation process shown in FIG. 5 in response to a predetermined condition being satisfied.

Examples of the predetermined condition include a condition that the detecting apparatus 1 is powered, and a condition that the detecting apparatus 1 is ready to communicate with the generating apparatus 2.

When the inclination information calculation process is started, the first controller 14 first calculates inclination angles of the detecting apparatus 1 (Step A1).

Figure 6A:
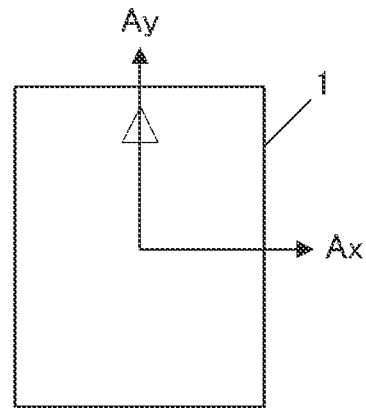
FIG. 6A shows X-axis and Y-axis of a three-axis acceleration sensor included in the radiation detecting apparatus.
Figure 6B:
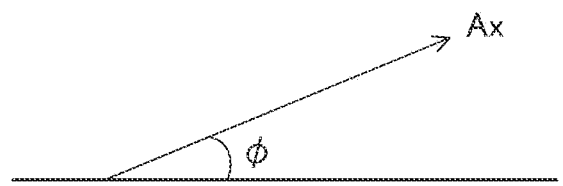
FIG. 6B shows inclination of the X-axis of the three-axis acceleration sensor with respect to the horizontal plane.
Figure 6C:
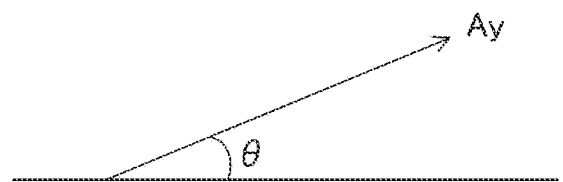
FIG. 6C shows inclination of the Y-axis of the three-axis acceleration sensor with respect to the horizontal plane.

More specifically, the first controller 14 calculates, as an inclination angle of the detecting apparatus 1, an inclination φ shown in FIG. 6B of the X-axis ("Ax" shown in FIG. 6A) of the three-axis acceleration sensor, which is the first sensor 17, with respect to the horizontal plane using the following equation (1). Also, the first controller 14 calculates, as an inclination angle of the detecting apparatus 1, an inclination θ shown in FIG. 6C of the Y-axis ("Ay" shown in FIG. 6A) of the three-axis acceleration sensor, which is the first sensor 17, with respect to the horizontal plane using the following equation (2).

[Formula 1]

$$\varnothing = a\tan(Ax/\sqrt{Ay^2 + Az^2}) \times 180/\pi \quad (1)$$

$$\theta = a\tan(Ay/\sqrt{Ax^2 + Az^2}) \times 180/\pi \quad (2)$$

The "Ax", "Ay" and "Az" are the X-, Y- and Z-directional components of gravitational acceleration, respectively.

Next, the first controller 14 determines the orientation of the detecting apparatus 1 from the gravitational acceleration output by the three-axis acceleration sensor (Step A2).

Figure 7A:
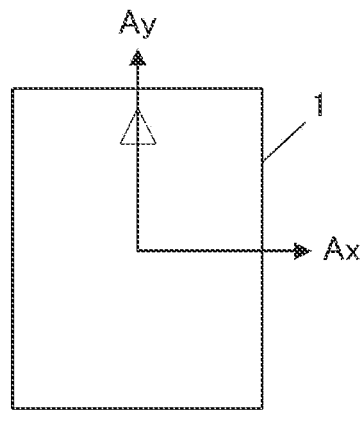
FIG. 7A to FIG. 7D show a method for determining orientation of the radiation detecting apparatus.

More specifically, the first controller 14 determines that the orientation of the detecting apparatus 1 is upward if |Ax|≤|Ay| and Ay≥0. The "upward" means that the detecting apparatus 1 is placed longitudinally long and a triangle (Δ) mark on the detecting apparatus 1 is pointing up, as shown in FIG. 7A.

Figure 7B:
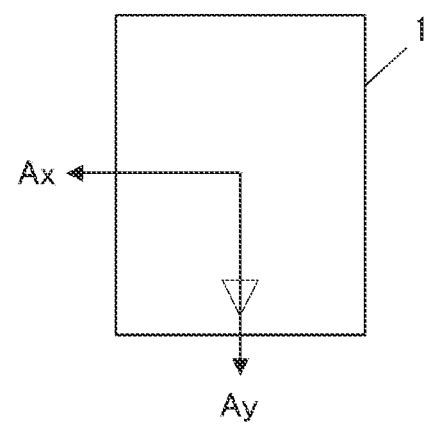

The first controller 14 determines that the orientation of the detecting apparatus 1 is downward if |Ax|≤|Ay| and Ay<0. The "downward" means that the detecting apparatus 1 is placed longitudinally long and the triangle mark on the detecting apparatus 1 is pointing down, as shown in FIG. 7B.

Figure 7C:
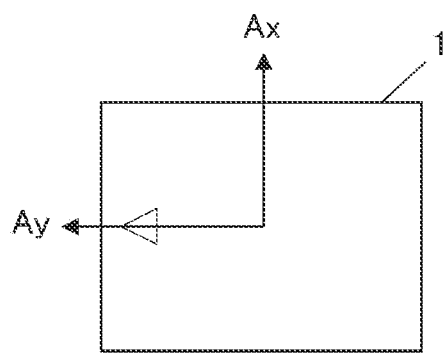

The first controller 14 determines that the orientation of the detecting apparatus 1 is 90 degrees to the left (leftward) if |Ax|>|Ay| and Ax>0. The "90 degrees to the left" means that the detecting apparatus 1 is placed laterally long and the triangle mark on the detecting apparatus 1 is pointing left, as shown in FIG. 7C.

Figure 7D:
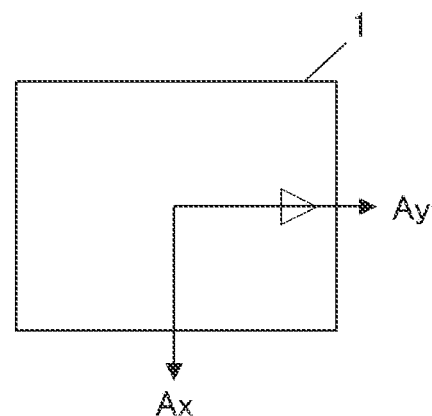

The first controller 14 determines that the orientation of the detecting apparatus 1 is 90 degrees to the right (rightward) if |Ax|>|Ay| and Ax≤0. The "90 degrees to the right" means that the detecting apparatus 1 is placed laterally long and the triangle mark on the detecting apparatus 1 is pointing right, as shown in FIG. 7D.

When the detecting apparatus 1 is placed horizontally, the gravitational accelerations in the X-axis and the Y-axis of the three-axis acceleration sensor are close to 0 G. As a result, the orientation of the detecting apparatus 1 cannot be determined correctly. Hence, the orientation of the detecting apparatus 1 placed horizontally is regarded as a predetermined orientation (upward in this embodiment), and when the inclination (inclination angle) of either the X-axis or the Y-axis reaches a certain angle (5 degrees in this embodiment), the first controller 14 performs Step A2 described above and Step A3 described below.

Next, the first controller 14 outputs the inclination information for the orientation of the detecting apparatus 1 determined in Step A2 (Step A3), and ends the inclination information calculation process.

More specifically, as shown in FIG. 8A and FIG. 9, if the orientation of the detecting apparatus 1 is upward, the first controller 14 outputs the inclination θ of the Y-axis with respect to the horizontal plane calculated in Step A1 as the roll angle of the detecting apparatus 1, and also outputs the inclination φ of the X axis with respect to the horizontal plane calculated in Step A1 as the pitch angle of the detecting apparatus 1.

As shown in FIG. 8B and FIG. 9, if the orientation of the detecting apparatus 1 is downward, the first controller 14 outputs the inclination -θ of the Y-axis with respect to the horizontal plane calculated in Step A1 with the opposite sign as the roll angle of the detecting apparatus 1, and also outputs the inclination -φ of the X-axis with respect to the horizontal plane calculated in Step A1 with the opposite sign as the pitch angle of the detecting apparatus 1.

As shown in FIG. 8C and FIG. 9, if the orientation of the detecting apparatus 1 is 90 degrees to the left, the first controller 14 outputs the inclination φ of the X-axis with respect to the horizontal plane calculated in Step A1 as the roll angle of the detecting apparatus 1, and also outputs the inclination -θ of the Y-axis with respect to the horizontal plane calculated in Step A1 with the opposite sign as the pitch angle of the detecting apparatus 1.

As shown in FIG. 8D and FIG. 9, if the orientation of the detecting apparatus 1 is 90 degrees to the right, the first controller 14 outputs the inclination -φ of the X-axis with respect to the horizontal plane calculated in Step A1 with the opposite sign as the roll angle of the detecting apparatus 1, and also outputs the inclination θ of the Y-axis with respect to the horizontal plane calculated in Step A1 as the pitch angle of the detecting apparatus 1.

Figure 10A:
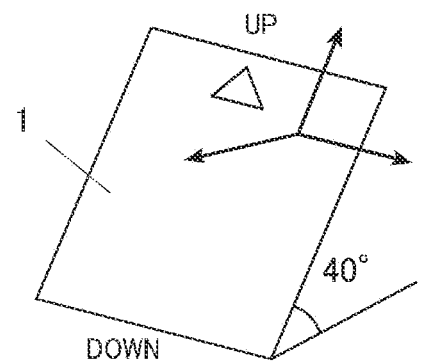
FIG. 10A to FIG. 10C each show arrangement of a radiation detecting apparatus and inclination information on the radiation detecting apparatus thereat in a conventional technique.
Figure 10B:
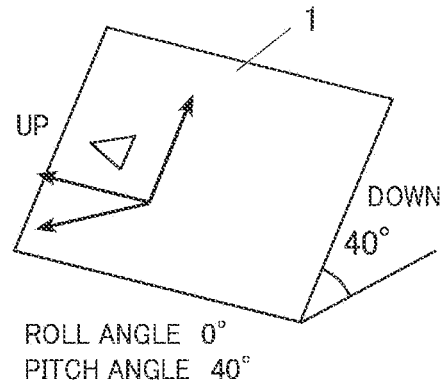

If the detecting apparatus 1 to be used has a size of 14×17 inches, although it is normally used, for example, in the state shown in FIG. 10A, it may be rotated, for example, 90 degrees (90 degrees to the left) as shown in FIG. 10B for imaging, depending on the physique of the subject S.

Figure 10C:
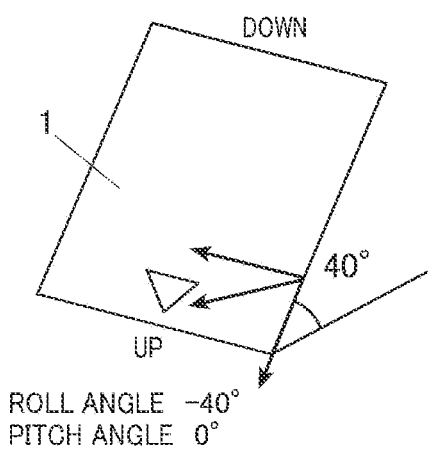

Further, since the detecting apparatus 1 is in the shape of a simple panel, the user U may take a picture of the subject S with the detecting apparatus 1 unintentionally upside down (rotated 180 degrees) as shown in FIG. 10C. In this case, the generated radiograph is also upside down, but it can be rotated.

If the detecting apparatus 1 is used by being rotated as described above, the relationship between the roll angle and the pitch angle is reversed, or the roll angle or the pitch angle is calculated as a negative value. This may cause a problem when the roll angle and the pitch angle of the tube 23 are finely adjusted.

Hence, in Step A3, the first controller 14 outputs the inclination information for the orientation of the detecting apparatus 1 determined in Step A2 in order not to cause the problem.

The first controller 14 may detect whether the radiation incident surface 1a of the detecting apparatus 1 faces the tube 23 (with the subject S in between) on the basis of the information on the gravitational acceleration in the Z-axis of the three-axis acceleration sensor, and if the radiation incident surface 1a of the detecting apparatus 1 does not face the tube 23, stops the process of Step A3 and call the user U's attention (e.g., performs control to display a warning).

After the detecting apparatus 1 is placed under or behind the subject S, it is usually impossible to be aware of whether the detecting apparatus 1 is not reversed in terms of the front side and the back side until imaging finishes. In the above manner, however, it is possible to check whether the detecting apparatus 1 is not reversed even while the detecting apparatus 1 is placed under or behind the subject S, thereby preventing imaging from failing and the subject S from unnecessarily being exposed to radiation R accordingly.

The inclination information calculation process may be performed by the second controller 211.

Figure 11:
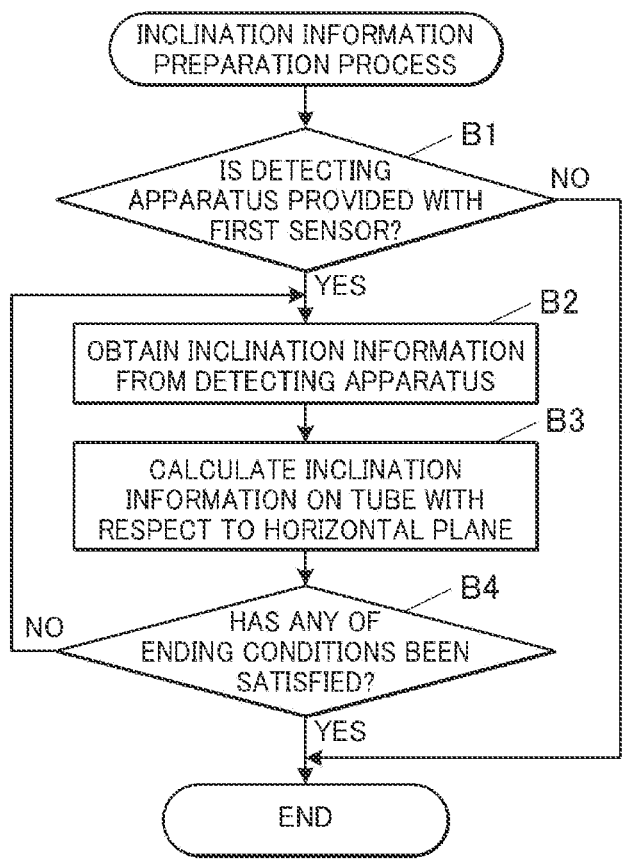
FIG. 11 is a flowchart of an inclination information preparation process that is performed by the radiation generating apparatus shown in FIG. 4.

The second controller 211 of the generating apparatus 2 (console 3) performs, for example, an inclination information preparation process shown in FIG. 11 in response to a predetermined condition being satisfied.

Examples of the predetermined condition include a condition that the generating apparatus 2 is powered, a condition that the generating apparatus 2 is ready to communicate with the detecting apparatus 1, and a condition that a predetermined operation is made on the operation unit 32 of the console 3.

(First Checking Process)

In the inclination information preparation process, the second controller 211 first performs a first checking process (Step B1).

In the first checking process, the second controller 211 determines information on the detecting apparatus 1 connected to itself (registered in the console 3).

Specifically, the second controller 211 checks whether the detecting apparatus 1 is provided with the first sensor 17.

More specifically, the second controller 211 determines whether the detecting apparatus 1 is provided with the first sensor 17, referring to information on presence or absence of the first sensor 17 stored in the detecting apparatus 1, a detecting apparatus ID stored in the detecting apparatus 1, collation information on the detecting apparatus 1 and presence or absence of the first sensor 17 stored in another apparatus (console 3, etc.), and/or the like.

If the second controller 211 determines in the first checking process that the detecting apparatus 1 is not provided with the first sensor 17 (Step B1; No), the second controller 211 ends the inclination information preparation process (allows no inclination information to be displayed).

If the second controller 211 determines therein that the detecting apparatus 1 is provided with the first sensor 17 (Step B1; Yes), the second controller 211 proceeds to the next process (Step B2) (allows the inclination information on the detecting apparatus 1 to be displayed).

By the second controller 211 performing the first checking process, when the detecting apparatus 1 not provided with the first sensor 17 is used, no inclination information is displayed. This can prevent the user U from recognizing wrong inclination information (i.e., inclination information on a different detecting apparatus 1).

By the second controller 211 performing the first checking process, when the detecting apparatus 1 provided with the first sensor 17 is used, the inclination information on the detecting apparatus 1 is displayed. This allows the user U to perform fine positioning.

Next, the second controller 211 obtains the inclination information on the detecting apparatus 1 from the detecting apparatus 1 (Step B2). More specifically, the second controller 211 obtains the inclination information for the orientation of the detecting apparatus 1 output in the inclination information calculation process (shown in FIG. 5).

Next, the second controller 211 calculates the inclination information (roll angle and pitch angle) on (of) the tube 23 with respect to the horizontal plane (Step B3). More specifically, the second controller 211 obtains, from the second sensor 27, three-axis directional components of gravitational acceleration detected by the second sensor 27. The second controller 211 then calculates the inclination information on the tube 23 on the basis of the three-axis directional components of gravitational acceleration detected by the second sensor 27.

Next, the second controller 211 performs an ending determination process (Step B4).

In the ending determination process of this embodiment, the second controller 211 determines whether at least one of the following ending conditions (1) and (2) has been satisfied.

(1) The emission instructing switch 22 is operated.
(2) Emission of radiation R finishes.

Because a radiograph to be generated is fixed when radiation R is emitted, there is little necessity thereafter to continue the inclination information preparation process or a display control process described below.

If the second controller 211 determines in the ending determination process that neither of the ending conditions has been satisfied (Step B4; No), the second controller 211 returns to Step B2. That is, the second controller 211 repeats Steps B2 and B3 until at least one of the ending conditions is satisfied.

If the second controller 211 determines therein that at least one of the ending conditions has been satisfied (Step B4; Yes), the second controller 211 ends the inclination information preparation process.

(Modification of Inclination Information Preparation Process)

In the inclination information preparation process, the second controller 211 may perform a state determination process after Step B3.

In the state determination process, the second controller 211 determines whether difference between first angle information (inclination information on the detecting apparatus 1 for the orientation of the detecting apparatus 1) and second angle information (inclination information on the tube 23) is within a predetermined reference range.

The second controller 211 may use this determination result as the inclination information on the detecting apparatus 1 and the tube 23.

Further, the second controller 211 may determine whether the SID measured by the distance measurer 29 is within a predetermined reference range.

In the case where the second controller 211 performs the state determination process, the second controller 211 may determine, before the state determination process, whether dynamic imaging is included in an imaging order received.

If the second controller 211 determines that dynamic imaging is included in the imaging order, the second controller 211 may change (narrow) a reference range that is used in the subsequent state determination process. Because dynamic imaging is used for dynamic analysis, alignment accuracy required therefor is higher as compared with the case where still images are generated.

In the case where the second controller 211 performs the state determination process, the second controller 211 may change the reference range depending on presence or absence of a grid and its type.

This is because as a grid ratio is greater, a radiograph to be generated is more likely to be affected by oblique incidence of radiation R (a generated radiograph has a greater density difference therein by being affected by cutoff due to a grid).

[3-3-2. Display Control of Inclination Information]

Figure 12:
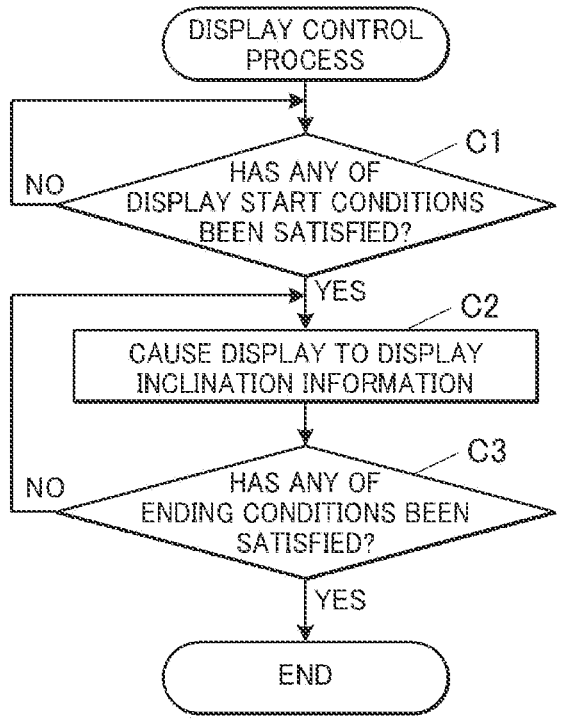
FIG. 12 is a flowchart of a display control process that is performed by the radiation generating apparatus shown in FIG. 4.

The second controller 211 performs, for example, the abovementioned display control process shown in FIG. 12 in response to start of repetition of the obtainment process of Step B2 and the calculation process of Step B3.

The second controller 211 performs the display control process in parallel with the inclination information preparation process.

(Condition Determination Process)

In the display control process, the second controller 211 first performs a condition determination process (Step C1).

In the condition determination process, the second controller 211 determines whether at least one of the following display start conditions (1) to (5) has been satisfied.

(1) An imaging order is selected on the console 3 that makes an instruction to start imaging.
(2) The detecting apparatus 1 is taken out from its storage place (e.g., the detecting apparatus storage 26 if the system 100 is a nursing cart, a charger cradle if the system 100 is installed in an imaging room, etc.).
(3) The detecting apparatus 1 is disconnected from a cable.
(4) A predetermined button (e.g., the lamp button to emit visible light to an area that is the irradiation field with radiation R) of the collimator 25, with which the tube 23 is provided, is operated.
(5) The degree of inclination of the detecting apparatus 1 is within a reference range (e.g., an angle difference between the tube 23 and the detecting apparatus 1 is smaller than a predetermined angle).

If the second controller 211 determines in the condition determination process that none of the display start conditions has been satisfied (Step C1; No), the second controller 211 repeats the condition determination process (waits until at least one of the display start conditions is satisfied).

If the second controller 211 determines therein that at least one of the display start conditions has been satisfied (Step C1; Yes), the second controller 211 proceeds to the next process (Step C2).

While the position and the orientation of the tube 23 are been roughly adjusted, the detecting apparatus 1 may not be placed under or behind the subject S yet, and hence the inclination information on the detecting apparatus 1 may not be helpful. If the inclination information is displayed at such a timing, it may confuse the user U (e.g., the user U may adjust the orientation of the tube 23 in conformity to the angle(s) of the detecting apparatus 1, the position of which has not been accurately adjusted yet). By the second controller 211 performing the condition determination process, the main display 31 and/or the sub-display 28 (which hereinafter may be referred to "display 28/31") display the inclination information after at least one of the display start conditions is satisfied. This can prevent the user U from being confused.

While the collimator 25 is emitting visible light, the detecting apparatus 1 is often placed under or behind the subject S because the positioning work is in the final stage. Hence, if the second controller 211 proceeds to the next step (Step C2) when the display start condition (4) is satisfied, the inclination information that is useful can be provided for the user U at a more appropriate timing.

As the display start conditions, which are, in the condition determination process, determined by the second controller 211 whether or not to be satisfied, the following display start conditions (6) to (8) may be included.

(6) After the detecting apparatus 1 is taken out from the detecting apparatus storage 26 (the inclination of the detecting apparatus 1 starts to change), the inclination of the detecting apparatus 1 becomes stable again (the detecting apparatus 1 is placed under or behind the subject S and no longer moves).
(7) A detection value of a barometric sensor that is included in the detecting apparatus 1 and detects air pressure inside the case of the detecting apparatus 1 exceeds a reference value (the detecting apparatus 1 is placed under or behind the subject S and its case is pressed).
(8) The detecting apparatus 1 is captured in an optical image generated by the optical camera of the distance measurer 29.

If the second controller 211 proceeds to the next process (Step C2) when the display start condition (6) or (7) is satisfied, the second controller 211 causes the display 28/31 to display the inclination information after the detecting apparatus 1 is placed under or behind the subject S, and hence can prevent the user U from being confused.

Further, the detecting apparatus 1 being in an area imaged by the optical camera of the distance measurer 29 means that the detecting apparatus 1 is likely to be placed under or behind the subject S right after that. Hence, if the second controller 211 proceeds to the next process (Step C2) when the display start condition (8) is satisfied, the second controller 211 causes the display 28/31 to display the inclination information at almost the same timing as the case where the second controller 211 proceeds to the next process (Step C2) when the display start condition (6) or (7) is satisfied, and hence can prevent the user U from being confused.

(Display Process)

After determining in the condition determination process that at least one of the display start conditions has been satisfied, the second controller 211 performs a display process (Step C2).

In the display process, the second controller 211 causes at least one of the main display 31 and the sub-display 28 to display the inclination information on the detecting apparatus 1 obtained in the obtainment process (Step B2) of the inclination information preparation process and the inclination information on the tube 23 calculated in the calculation process (Step B3) thereof.

Figure 13:
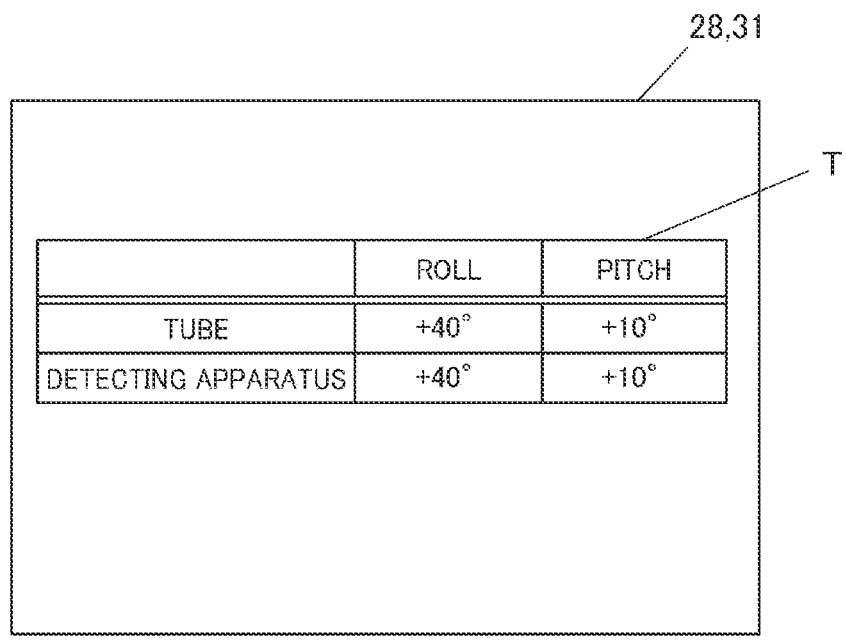
FIG. 13 shows an example of a screen that is displayed by the radiation generating apparatus or the console shown in FIG. 4.
Figure 14:
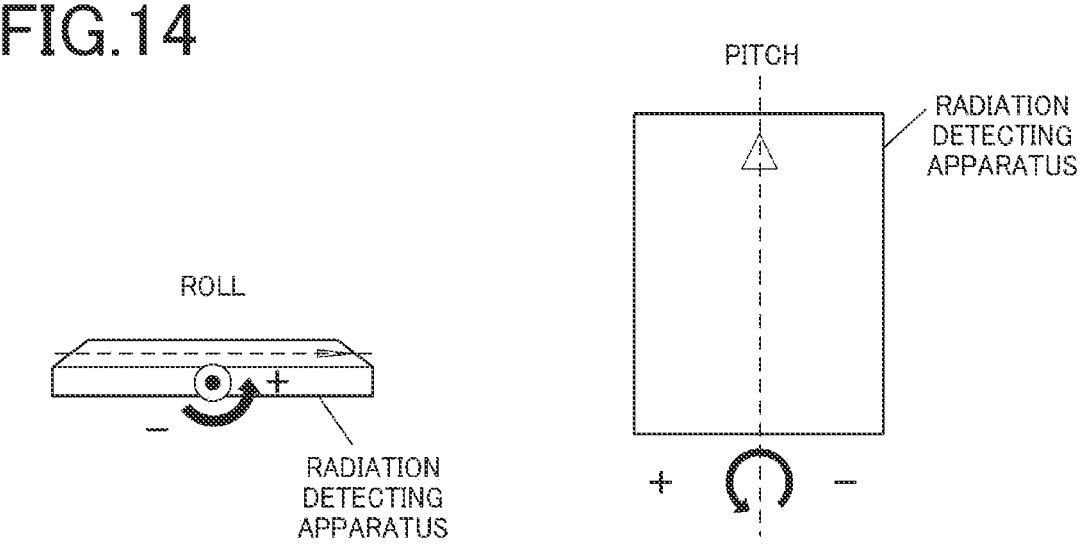
FIG. 14 shows the roll and the pitch of the radiation detecting apparatus when the orientation thereof is upward.
Figure 15A:
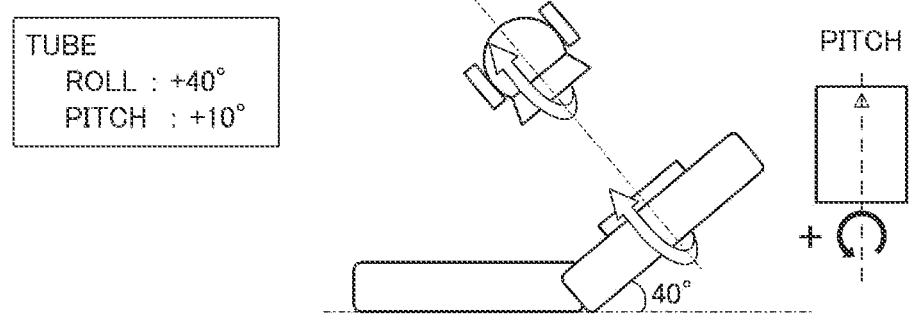
FIG. 15A and FIG. 15B show an example of a display mode of the inclination information on a tube and the inclination information on a detecting apparatus that are displayed by a radiation generating apparatus or a console in a conventional technique.
Figure 15B:
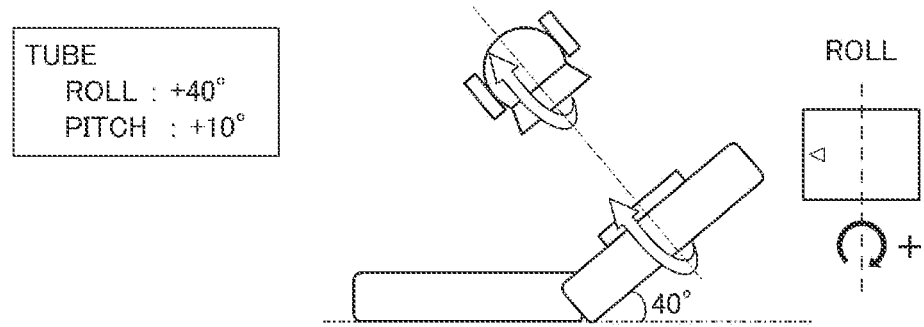

More specifically, as shown in FIG. 13, in a table T, the roll angle (e.g., "+40°") and the pitch angle (e.g., "+10°") of the tube 23 and the roll angle (e.g., "+40°") and the pitch angle (e.g., "+10°") of the detecting apparatus 1 are displayed. As to the angles of the detecting apparatus 1, the displayed values are based on the inclination information on the detecting apparatus 1 for the orientation of the detecting apparatus 1. Hence, for example, even if the orientation of the detecting apparatus 1 is changed from upward (shown in FIG. 15A) to 90 degrees to the left (shown in FIG. 15B), the values of the roll angle and the pitch angle of the detecting apparatus 1 are displayed with no change.

If the inclination information (i.e., the inclination information on the detecting apparatus 1 and the inclination information on the tube 23) is displayed by the sub-display 28, the user U can refer to the inclination information when and where he/she finely adjusts the position and the orientation of the tube 23. This allows the user U to easily perform the fine adjustment.

If the inclination information is displayed by the main display 31, the user U can do the final checking when (and where) he/she operates the emission instructing switch 22 as to whether the positional relationship between the detecting apparatus 1 and the tube 23 has unchanged.

The second controller 211 may perform control to display the roll angle and the pitch angle of the detecting apparatus 1 in the form of differences from the roll angle and the pitch angle of the tube 23, respectively.

The second controller 211 updates the inclination information, which is displayed, each time the second controller 211 performs the obtainment process (Step B2) and the calculation process (Step B3) of the inclination information preparation process.

In this manner, the user U can check the inclination information in real time.

The second controller 211 may cause the display 28/31 to display the inclination information before any of the display start conditions is satisfied.

In this case, it is preferable that the second controller 211 change the display mode of the inclination information to the following.
  (i) Instead of causing the display 28/31 to display or not display the inclination information, the second controller 211 changes the display color of the inclination information between before and after the detecting apparatus 1 is taken out from the detecting apparatus storage 26 (e.g., performs control to display the inclination information in gray (light color) before the detecting apparatus 1 is taken out from the detecting apparatus storage 26, and performs control to display the inclination information in a darker (standard) color after the detecting apparatus 1 is taken out therefrom); and/or
  (ii) The second controller 211 performs control to display, in addition to the inclination information, a message that the detecting apparatus 1 is stored in the detecting apparatus storage 26 or in a sleep state.

These can prevent the user U from being confused as in the case where the second controller 211 causes the display 28/31 to display the inclination information only after at least one of the display start conditions is satisfied.

If the second controller 211 proceeds to the next step (Step C2) when at least one of the display start conditions except the display start condition (4) is satisfied (i.e., causes the display 28/31 to display the inclination information before the predetermined button of the collimator 25 is operated), the second controller 211 may change the display mode of the inclination information, which is displayed by the display 28/31, for the period in which the collimator 25 is emitting visible light to the area that is the irradiation field.

More specifically, the inclination information is enlarged or displayed as a pop-up for the abovementioned period. This makes it easier for the user U to see the inclination information as compared with the inclination information displayed before the emission.

In the case where the second controller 211 performs the state determination process in the inclination information preparation process, the second controller 211 may cause the display 28/31 to display the determination result in the display process. In this manner, the user U can easily perform fine adjustment of the position and the orientation of the tube 23.

In this case, the second controller 211 may perform, if the state of the tube 23 and the detecting apparatus 1 facing one another is within a reference range, control to display a message indicating this fact, but if the state thereof is outside the reference range, control not to display any message. This is because, in the case where the detecting apparatus 1 is placed under or behind the subject S after the position and the orientation of the tube 23 are roughly adjusted, if the display 28/31 keeps displaying a message indicating that the state is outside the reference range while the position and the orientation of the tube 23 are being roughly adjusted, it confuses the user U. The above, on the other hand, can prevent the user U from being confused.

The second controller 211 may cause the display 28/31 to display a predetermined color, and cause the display 28/31 to change the color to another when the state of the tube 23 and the detecting apparatus 1 facing one another enters the reference range.

Alternatively or additionally, the second controller 211 may cause a not-shown speaker to output a predetermined sound when the state of the tube 23 and the detecting apparatus 1 facing one another enters the reference range.

The second controller 211 may cause the display 28/31 to display the determination result only while the collimator 25 is emitting visible light to the area that is the irradiated field.

During a period in which the collimator 25 is not emitting visible light, the detecting apparatus 1 is likely to be still stored in the detecting apparatus storage 26 or placed on a desk or the like. In contrast, during a period in which the collimator 25 is emitting visible light, the positioning work is in the final stage. Hence, the above can provide the determination result for the user U at a more appropriate timing.

The above-described control to display the determination result in the state determination process is applicable to the determination result as to whether the SID (or SSD) is within the reference range.

In the display control process of this embodiment, the second controller 211 performs an ending determination process (Step C3) after the inclination information starts to be displayed.

In the ending determination process, the second controller 211 determines whether at least one of the following ending conditions (1) to (3) has been satisfied.
  (1) The emission instructing switch 22 is operated.
  (2) Emission of radiation R finishes.
  (3) The inclination information preparation process finishes.

If the second controller 211 determines in the ending determination process that none of the ending conditions has been satisfied (Step C3; No), the second controller 211 returns to Step C2. That is, the second controller 211 causes the display 28/31 to keep displaying the inclination information until at least one of the ending conditions is satisfied.

If the second controller 211 determines that at least one of the ending conditions has been satisfied (Step C3; Yes), the second controller 211 ends the display control process.

(First Modification of Display Control Process)

In the display control process, the second controller 211 may perform a second checking process before starting the condition determination process.

In the second checking process, the second controller 211 determines whether the detecting apparatus 1 has received an instruction from the console 3 to start imaging.

If more than one detecting apparatus 1 is registered in the console 3 (stored in the detecting apparatus storage 26), the second controller 211 performs the second checking process for each detecting apparatus 1.

In the subsequent display process, the second controller 211 causes the display 28/31 to display the inclination information on the detecting apparatus 1 that has received an instruction from the console 3 to start imaging.

There is a case where a nursing cart is provided with two or more detecting apparatuses of different sizes. If the inclination information on each of the detecting apparatuses 1 including a detecting apparatus(es) 1 not to be used is displayed at the same time, it confuses the user U. The second controller 211 performing the second checking process allows the user U to easily know which detecting apparatus 1's inclination information is currently displayed.

(Second Modification of Display Control Process)

In the display control process, when the second controller 211 causes the display 28/31 to display the inclination information before imaging of the subject S (during preparation), the second controller 211 may cause the display 28/31 to display, together with it, previous inclination information at the time of previous imaging of the subject S.

More specifically, the second controller 211 calls the previous inclination information on the basis of the ID of the subject S, and causes the display 28/31 to display it too.

In this case, it is preferable that the second controller 211 call the previous inclination information on the basis of the ID of the subject S and the imaging part (chest, abdomen, etc.). This is because the detecting apparatus 1 may be inclined differently depending on the imaging part.

If the inclination of the tube 23 or the subject S changes every time imaging is performed, difference is generated in positions of structures in the body of the subject S and accordingly generated in density between generated radiographs. This change (and difference) could be a factor to overlook a small change in a follow-up. Displaying the previous inclination information improves positioning reproducibility and can reduce the risk of overlooking a small change.

The second controller 211 may cause the display 28/31 to display the previous inclination information and the SID (or SSD) by overlaying these on a radiograph. This makes it possible to use a limited display space effectively, and also can reduce movement of the line of sight between the radiograph and the previous inclination information or the like during preparation for imaging or diagnosis.

If imaging being currently prepared is decubitus imaging or standing imaging, the second controller 211 may cause the display 28/31 not to display the previous inclination information. This is because it is obvious that the angle φ formed by the horizontal plane and the radiation incident surface 1a is 0° in decubitus imaging or 90° in standing imaging, and displaying the previous inclination information rather confuses the user U.

[3-3-3. Generation/Emission of Radiation]

The second controller 211 sends an emission instruction signal to the generator 213 to instruct the generator 213 to generate/emit radiation R in a mode suitable for the form of a radiograph(s) to be generated (still image or dynamic image composed of a plurality of frames) in response to receiving an operation signal from the emission instructing switch 22 (an operation on the emission instructing switch 22).

The generator 213, which has received the emission instruction signal from the second controller 211, applies voltage and flows current according to the preset imaging conditions to the tube 23.

The tube 23, which has received the voltage and the current from the generator 213, generates/emits a dose of radiation R corresponding to the voltage and the current in a mode suitable for the voltage and the current.

In the case of still images, the tube 23 emits radiation R once per press on the emission instructing switch 22.

In the case of dynamic images, the tube 23 repeats emission of pulsed radiation R multiple times per predetermined time (e.g., 15 times per second) or keeps emitting radiation R for a predetermined time, per press on the emission instructing switch 32.

[3-3-4. Storing of Inclination Information]

After radiation R is emitted (imaging is performed), the second controller 211 performs a storing process.

In the storing process, the second controller 211 stores the inclination information at the time of imaging of the subject S together with the information on the subject S.

Examples of the method for storing the inclination information include a method of writing the inclination information in the header of the generated radiograph, and a method of linking the inclination information with the generated radiograph and storing same in the second memory 212 or a memory of another apparatus (PACS, etc.).

In the storing process, the second controller 211 may store not only the inclination information but also the SID (or SSD) at the time of imaging of the subject S. This makes it possible to check the SID at the time of the previous imaging of the subject S when another imaging of the subject S is performed, and hence can reproduce the positions and the orientations of the detecting apparatus 1 and the tube 23 with a high degree of accuracy when another imaging is performed.

In particular, writing the inclination information together with or without the SID in the header of the generated radiograph (linking the inclination information with the generated radiograph) makes it possible to manage the inclination information more effectively, and also can make the inclination information more useful for diagnosis (e.g., makes it easier for a diagnostician to imagine where the structures in the body of the subject S are supposed to be).

In the case of imaging in which a plurality of radiographs is generated by one imaging operation (e.g., dynamic imaging), the second controller 211 may store, in the storing process, the inclination information (a piece of inclination information) each time one radiograph (frame) is obtained.

In this manner, the user U and a diagnostician can compare the pieces of inclination information associated with the respective radiographs with one another to check whether a significant body movement has occurred during imaging.

Further, referring to the pieces of inclination information makes it easy to automatically delete an abnormal radiograph(s) among the generated radiographs or exclude it from a list of radiographs to be analyzed.

Still further, displaying the piece(s) of inclination information with the radiograph(s) makes it possible to call the diagnostician's attention.

In the case where the inclination information (a piece of inclination information) is stored each time a radiograph is obtained, the second controller 211 may perform a determination process in the storing process.

In the determination process, the second controller 211 determines representative (piece of) inclination information that is representative of imaging on the basis of the pieces of inclination information, each of which is stored each time a radiograph is obtained.

Examples of the "representative inclination information that is representative of imaging" include the inclination information at the time of generation of a predetermined ordinal number of a radiograph (e.g., the first radiograph) among radiographs, the average value of all the pieces of inclination information, the median value of all the pieces of inclination information, and the average value of some of all the pieces of inclination information (e.g., the average value of the inclination information at the time of generation of the first radiograph and the inclination information at the time of generation of the last radiograph).

Works using a plurality of pieces of inclination information are complicated works for the user U and a diagnostician. The above, however, allows the user U or a diagnostician to use only the representative inclination information as a reference at the time of positioning or diagnosis, and accordingly can reduce the user U's or the diagnostician's time and effort.

The average value or the like being the representative inclination information produces the representative inclination information in which the imaging state is more accurately reflected.

The average value, the median value or the like being the representative inclination information, which is used as a reference at the time of positioning or diagnosis, can eliminate influence of variation in the (pieces of) inclination information due to respiration or the like on positioning or diagnosis.

[3-3-5. First Modification of Operation of Radiation Generating Apparatus]

In the above embodiment, the second controller 211 causes the display 28/31 to display the inclination information if at least one of the display start conditions is satisfied while the second controller 211 is repeatedly performing the obtainment process (Step B2) and the calculation process (Step B3), but may start the obtainment process and the calculation process in response to at least one of the display start conditions being satisfied. As compared with the case where the second controller 211 performs the obtainment process and the calculation process before at least one of the display start conditions is satisfied, this can reduce power consumption of the second controller 211.

In this case, the second controller 211 may store the inclination information without causing the display 28/31 to display the inclination information even after the second controller 211 starts the obtainment process and the calculation process. In such a case, for example, presence or absence of an abnormality during imaging can be checked by checking the inclination information, for example, when maintenance is performed.

[3-3-6. Second Modification of Operation of Radiation Generating Apparatus]

Nursing carts of the same type may have slightly different inclination angles of detecting apparatus storages 26 due to, for example, individual difference in distortion of cases that the respective nursing carts have.

Hence, the second controller 211 of each nursing cart may correct (calibrate) the detection value of the first sensor 17 received from the detecting apparatus 1 stored in the detecting apparatus storage 26.

More specifically, the second controllers 211 of the respective nursing carts correct their respective output values (detection values) so as to indicate that the rotation angles of the detecting apparatuses 1 stored in the detecting apparatus storages 26 with respect to the horizontal plane are all the same inclination angles.

4. Advantageous Effects

As described above, the detecting apparatus 1 of the above embodiment detects rotation angles (inclination angles) of itself with respect to two mutually perpendicular axes (X-axis, Y-axis) to output inclination information (roll angle and pitch angle). The detecting apparatus 1 also detects the orientation of itself. The detecting apparatus 1 outputs the inclination information for the detected orientation.

Thus, by outputting the inclination information for the orientation, the detecting apparatus 1 can make the values of the roll angle and the pitch angle of itself, which are to be output, unchanged even if the orientation of the detecting apparatus 1 is changed. This makes it possible to easily perform angle adjustment of the tube 23 and the detecting apparatus 1 regardless of the orientation of the detecting apparatus 1.

5. Others

It goes without saying that the present disclosure is not limited to the above embodiment or the like and can be appropriately modified without departing from the scope of the present disclosure.

For example, in the above, a hard disk, a nonvolatile semiconductor memory or the like is used as a computer-readable medium storing the program(s) of the present disclosure. However, this is not a limitation. The computer-readable medium may be a portable recording medium, such as a CD-ROM. Further, as a medium to provide data of the program(s) of the present disclosure via a communication line, a carrier wave can be used.

Although one or more embodiments or the like of the present disclosure have been described and illustrated in detail, the disclosed embodiments or the like are made for purposes of not limitation but illustration and example only. The scope of the present disclosure should be interpreted by terms of the appended claims.

The invention claimed is:

1. An X-ray radiation detecting apparatus that detects X-ray radiation transmitted through a subject, comprising a hardware processor that
    detects rotation angles of the X-ray radiation detecting apparatus with respect to two mutually perpendicular axes to output angle information of the X-ray radiation detecting apparatus, and
    detects an orientation of the X-ray radiation detecting apparatus,
    wherein the hardware processor outputs the angle information for the detected orientation,
    the rotation angles are two inclination angles with respect to the two mutually perpendicular axes, the two mutually perpendicular axes are on a horizontal plane, and the angle information includes the two inclination angles of the X-ray radiation detecting apparatus.

2. The X-ray radiation detecting apparatus according to claim 1, wherein the hardware processor outputs the angle information to an external apparatus.

3. The X-ray radiation detecting apparatus according to claim 1, wherein the rotation angles and the orientation are detected based on gravitational acceleration output by a three-axis acceleration sensor.

4. The X-ray radiation detecting apparatus according to claim 1, wherein the hardware processor detects the orientation in response to outputting predetermined inclination angles of the X-ray radiation detecting apparatus with respect to the two mutually perpendicular axes as the angle information.

5. The X-ray radiation detecting apparatus according to claim 1, wherein the hardware processor outputs, as the angle information, roll and pitch angles of the X-ray radiation detecting apparatus into which the detected rotation angles are converted according to the orientation.

6. A radiographic imaging system comprising:
an X-ray radiation emitting apparatus that emits X-ray radiation;
an X-ray radiation detecting apparatus that detects the X-ray radiation transmitted through a subject; and
a hardware processor that
    detects rotation angles of the X-ray radiation detecting apparatus with respect to two mutually perpendicular axes to output angle information of the X-ray radiation detecting apparatus, and
    detects an orientation of the X-ray radiation detecting apparatus,
wherein the hardware processor outputs the angle information for the detected orientation, and wherein the hardware processor causes a display to display the output angle information, the rotation angles are two inclination angles with respect to the two mutually perpendicular axes, the two mutually perpendicular axes are on a horizontal plane, and the angle information includes the two inclination angles of the X-ray radiation detecting apparatus.

7. The radiographic imaging system according to claim 6, wherein the display is included in the X-ray radiation emitting apparatus.

8. The radiographic imaging system according to claim 6, wherein rotation angles of an X-ray radiation source of the X-ray radiation emitting apparatus are adjustable.

9. The radiographic imaging system according to claim 6, wherein the hardware processor outputs, as the angle information, roll and pitch angles of the X-ray radiation detecting apparatus into which the detected rotation angles are converted according to the orientation.

10. An inclination angle outputting method for an X-ray radiation detecting apparatus that detects X-ray radiation transmitted through a subject, comprising:
(i) detecting rotation angles of the X-ray radiation detecting apparatus with respect to two mutually perpendicular axes to output angle information of the X-ray radiation detecting apparatus; and
(ii) detecting an orientation of the X-ray radiation detecting apparatus,
wherein the (i) detecting includes outputting the angle information for the detected orientation, the rotation angles are two inclination angles with respect to the two mutually perpendicular axes, the two mutually perpendicular axes are on a horizontal plane, and the angle information includes the two inclination angles of the X-ray radiation detecting apparatus.

* * * * *